(12) United States Patent
Masahashi et al.

(10) Patent No.: US 12,714,380 B2
(45) Date of Patent: Aug. 25, 2026

(54) X-RAY DIAGNOSIS APPARATUS AND DISINFECTION METHOD USING X-RAY DIAGNOSIS APPARATUS

(71) Applicant: Canon Kabushiki Kaisha, Tokyo (JP)

(72) Inventors: Junji Masahashi, Otawara (JP); Seiichiro Nagai, Otawara (JP); Nobuo Kobayashi, Nasushiobara (JP); Daisuke Takahashi, Otawara (JP); Norimitsu Kosugi, Nasushiobara (JP); Atsushi Kotani, Nasushiobara (JP); Yusuke Okumura, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 756 days.

(21) Appl. No.: 17/807,789

(22) Filed: Jun. 20, 2022

(65) Prior Publication Data

US 2022/0401047 A1 Dec. 22, 2022

(30) Foreign Application Priority Data

Jun. 21, 2021 (JP) ................................. 2021-102719
May 6, 2022 (JP) ................................. 2022-076776

(51) Int. Cl.
*A61B 6/00* (2024.01)
*A61L 2/10* (2026.01)
(Continued)

(52) U.S. Cl.
CPC .......... *A61B 6/4423* (2013.01); *A61B 6/4405* (2013.01); *A61B 6/547* (2013.01);
(Continued)

(58) Field of Classification Search
CPC . A61L 2/10; A61L 2/24; A61B 6/4423; A61B 6/4405; A61B 6/547
See application file for complete search history.

(56) References Cited

U.S. PATENT DOCUMENTS 6,605,260 B1 8/2003 Busted
9,345,798 B2 5/2016 Trapani
(Continued)

FOREIGN PATENT DOCUMENTS

JP 2002-512086 A 4/2002
JP 2006-129949 A 5/2006
(Continued)

*Primary Examiner* — Donald R Spamer
*Assistant Examiner* — Kayla Rose Sarantakos
(74) *Attorney, Agent, or Firm* — Oblon, McClelland, Maier & Neustadt, L.L.P.

(57) ABSTRACT

An x-ray diagnosis apparatus according to an embodiment includes an x-ray tube holder, a supporter, an ultraviolet ray, a contact portion detector, and an irradiation controller. The x-ray tube holder holds an x-ray tube. The supporter movably supports the x-ray tube holder. The ultraviolet ray emitter is disposed to the x-ray tube holder and emits ultraviolet rays. The contact portion detector detects a contact portion touched by a subject of detection, which is at least one of a subject of examination and an examination technician. The irradiation controller controls the support to move the x-ray tube holder to a position corresponding to the contact portion, and controls the ultraviolet ray emitter to emit the ultraviolet rays toward the contact portion.

11 Claims, 17 Drawing Sheets

(51) Int. Cl.
*A61L 2/24* (2006.01)
*A61L 103/15* (2026.01)

(52) U.S. Cl.
CPC .................................... *A61L 2/10* (2013.01); *A61L 2/24* (2013.01); *A61B 6/4464* (2013.01); *A61L 2103/15* (2026.01); *A61L 2202/11* (2013.01); *A61L 2202/14* (2013.01)

(56) References Cited

U.S. PATENT DOCUMENTS

| | | | | |
|---|---|---|---|---|
| 2017/0360386 | A1* | 12/2017 | Ninomiya | A61B 6/4405 |
| 2019/0117812 | A1* | 4/2019 | Olsen | A61L 2/26 |
| 2021/0252179 | A1* | 8/2021 | Grinstead | A61L 2/24 |

FOREIGN PATENT DOCUMENTS

| | | | | | |
|---|---|---|---|---|---|
| JP | 2017-124220 | A | | 7/2017 | |
| KR | 20150091032 | A | * | 8/2015 | A61B 6/00 |

* cited by examiner

X-RAY DIAGNOSIS APPARATUS AND DISINFECTION METHOD USING X-RAY DIAGNOSIS APPARATUS

CROSS REFERENCE TO RELATED APPLICATIONS

This application is based upon and claims the benefit of priority from the prior Japanese Patent Applications No. 2021-102719, filed on Jun. 21, 2021, and No. 2022-076776, filed on May 6, 2022 the entire contents of which are incorporated herein by reference.

FIELD

Embodiments disclosed herein and the accompanying drawings relate to an x-ray diagnosis apparatus and a disinfection method using the x-ray diagnosis apparatus.

BACKGROUND

In a hospital, it may be required that any place in an x-ray examination room touched by a patient be disinfected every time an x-ray examination is performed, in order to prevent virus infection in the hospital. An ultraviolet ray emitter configured to emit ultraviolet rays (UV-C; short wavelength ultraviolet rays) may be used for automatically disinfect the x-ray examination room. However, most of the ultraviolet ray emitters used for such a purpose are of fixed type, and used for disinfecting the entire x-ray examination room. This requires much time.

If the x-ray diagnosis apparatus is disinfected by a radiological technologist or a nurse within a limited time between x-ray examinations, there may be an area that is left non-disinfected.

DETAILED DESCRIPTION

Embodiments will now be described with reference to the accompanying drawings. It should be noted that the present invention is not limited to the embodiments described below.

An x-ray diagnosis apparatus according to an embodiment includes an x-ray tube holder, a supporter, an ultraviolet ray, a contact portion detector, and an irradiation controller. The x-ray tube holder holds an x-ray tube. The supporter movably supports the x-ray tube holder. The ultraviolet ray emitter is disposed to the x-ray tube holder and emits ultraviolet rays. The contact portion detector detects a contact portion touched by a subject of detection, which is at least one of a subject of examination and an examination technician. The irradiation controller controls the supporter to move the x-ray tube holder to a position corresponding to the contact portion, and controls the ultraviolet ray emitter to emit the ultraviolet rays toward the contact portion.

First Embodiment

Figure 1:
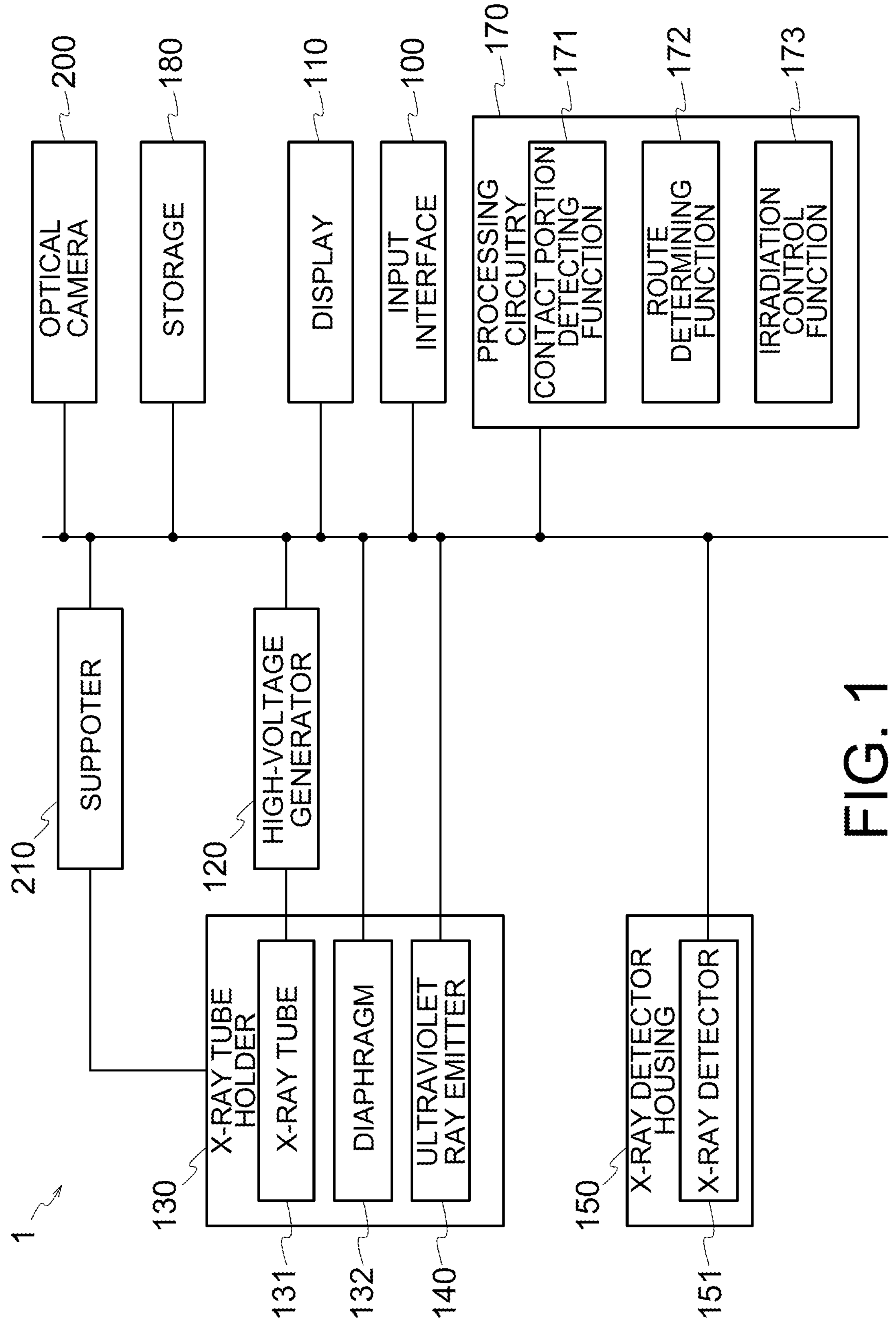
FIG. 1 is a block diagram showing a configuration of an x-ray diagnosis apparatus according to a first embodiment.
Figure 2:
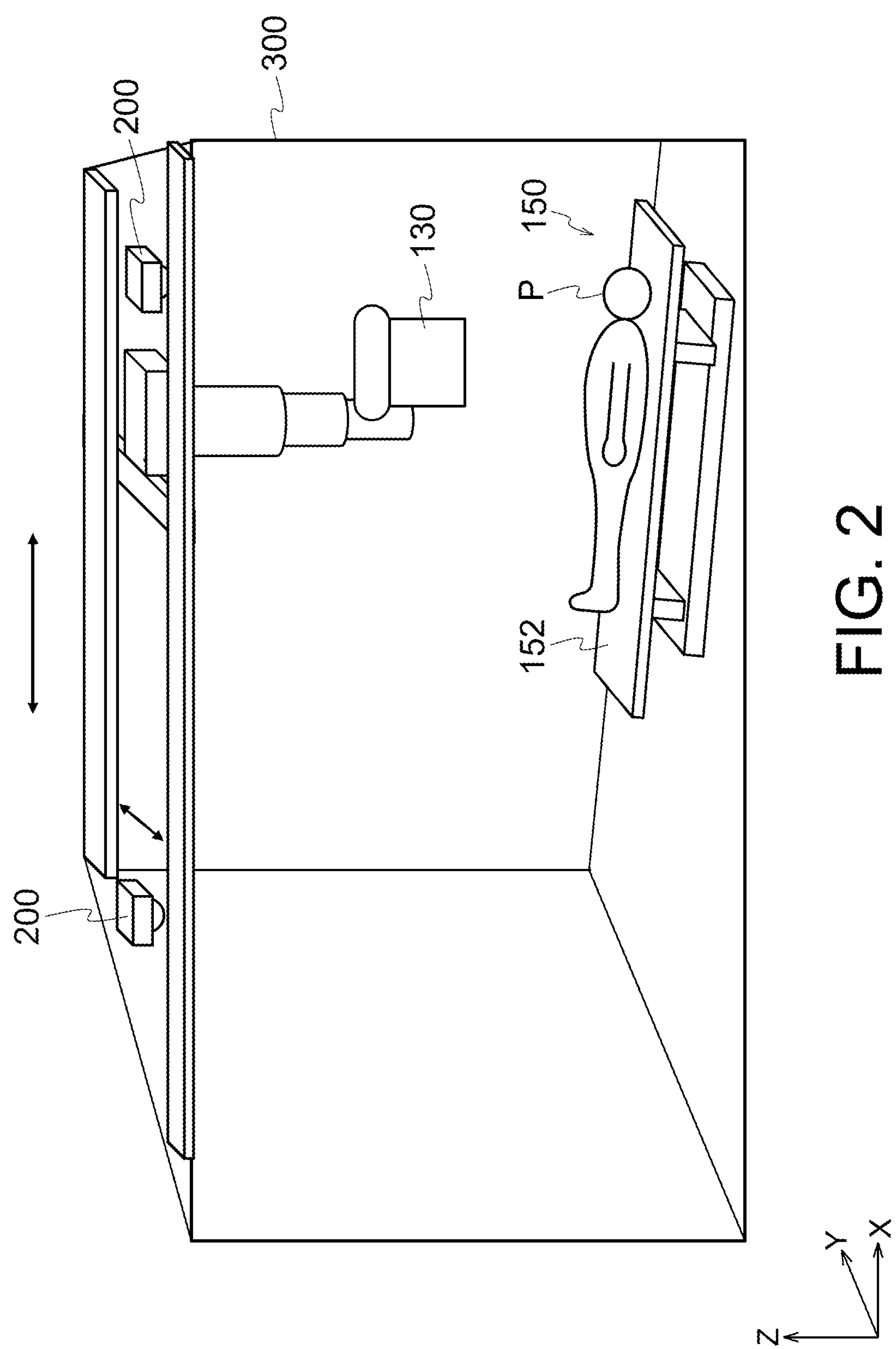
FIG. 2 is a schematic diagram of an examination room used for x-ray examination.

FIG. 1 is a block diagram showing a configuration of an x-ray diagnosis apparatus according to a first embodiment. FIG. 2 is a schematic diagram of an examination room used for x-ray examination.

As illustrated in FIG. 1, the x-ray diagnosis apparatus 1 according to the first embodiment includes an x-ray tube holder 130, a supporter 210, a high-voltage generator 120, an x-ray detector housing 150, an optical camera 200, processing circuitry 170, an input interface 100, a display 110, and a storage 180.

The components of the x-ray diagnosis apparatus 1 are connected with each other via a local area network (LAN). As shown in FIG. 2, the optical camera 200 and the supporter 210 are disposed in an examination room 300 in which an x-ray examination is performed. The x-ray tube holder 130 and the x-ray detector housing 150 are also disposed in the examination room 300.

The optical camera 200 is placed on a ceiling 301 of the examination room 300, for example. The optical camera 200 is, for example, a monitoring camera such as an industrial television (ITV) camera. Image information obtained by the optical camera 200 shows the state in the examination room 300. The optical camera 200 sends the image information to the processing circuitry 170.

In the first embodiment, two optical cameras 200 are mounted on the ceiling 301 of the examination room 300. The number and the locations of optical cameras 200 are arbitrarily determined depending on the dimensions of the examination room 300 and the area that may be touched a patient.

The supporter 210 is a supporting mechanism for movably supporting the x-ray tube holder 130. The supporter 210 supports the x-ray tube holder 130 so as to be movable in a horizontal direction (XY direction) and a vertical direction (Z direction). The supporter 210 also rotatably supports the x-ray tube holder 130. The horizontal, vertical, and rotational movements of the x-ray tube holder 130 are activated by driving mechanisms disposed to the supporter 210.

The input interface 100 is for inputting a signal or information corresponding to an operation performed by an examination technician such as a radiological technologist The input interface 100 is, for example, a pointing device such as a keyboard, a mouse device, or a switch such as an x-ray emission switch.

The display 110 is controlled by the processing circuitry 170 to display images. The display 110 is, for example, a display device such as a liquid crystal display or an organic electro-luminescence (EL) display.

The high-voltage generator 120 is controlled by the processing circuitry 170 to generate a high voltage and apply the generated high voltage to the x-ray tube holder 130. The x-ray tube holder 130 holds the x-ray tube 131. The x-ray tube holder 130 includes the x-ray tube 131, a diaphragm 132, an x-ray emission window 133, and ultraviolet ray emitters 140. The x-ray tube 131 emits x-rays in response to the high voltage applied by the high-voltage generator 120.

The diaphragm 132 has diaphragm blades including, for example, a pair of blades disposed at the top and the bottom of the diaphragm and a pair of blades disposed at the left side and the right side of the diaphragm (total four blades). Each of the diaphragm blades is a flat plate formed of a material that blocks x-rays, such as lead. The diaphragm 132 is controlled by the processing circuitry 170 to open or close the diaphragm blades to define an irradiated area (field of irradiation) irradiated with the x-rays emitted from the x-ray tube 131.

The ultraviolet ray emitters 140 are, for example, deep ultraviolet light emitting diodes (LED). The ultraviolet ray emitters 140 are controlled by the processing circuitry 170 to emit deep ultraviolet (UV-C) lays having a short wavelength (100 to 280 nm).

Figure 3:
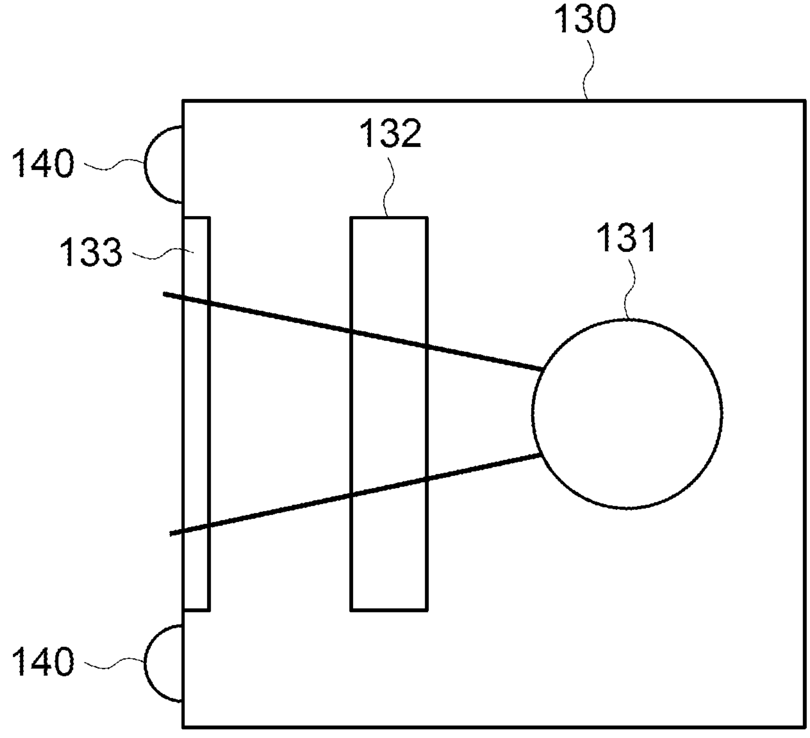
FIG. 3 is a simplified side view of an x-ray tube holder according to the first embodiment.
Figure 4:
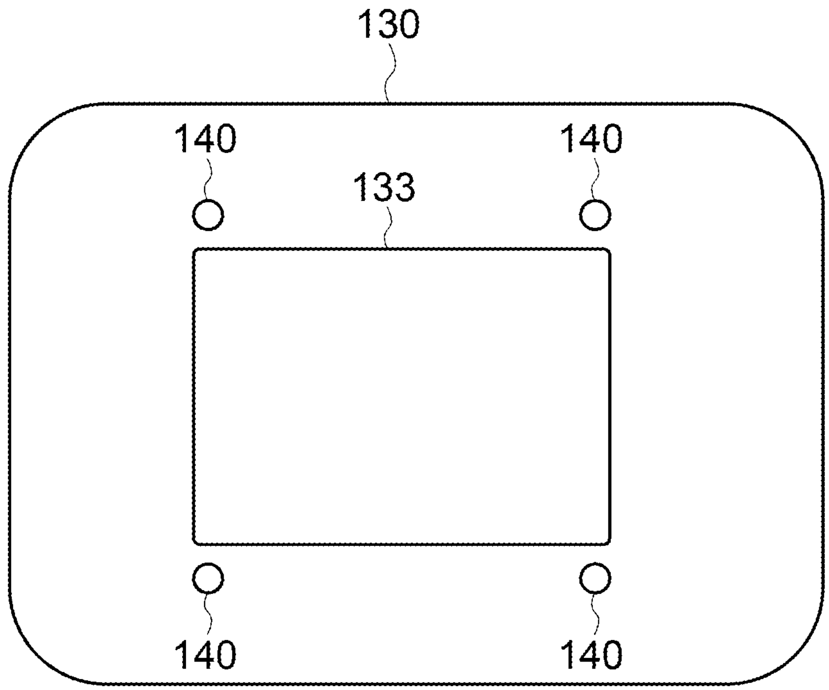
FIG. 4 is a front view of the x-ray tube holder according to the first embodiment, viewed from the side toward which x-rays are emitted.

FIG. 3 is a simplified side view of the x-ray tube holder 130. FIG. 4 is a front view of the x-ray tube holder 130 viewed from the side toward which x-rays are emitted. As shown in FIG. 3, the ultraviolet ray emitters 140 are arranged to surround the x-ray emission window 133. As shown in FIG. 4, four ultraviolet ray emitters 140 are disposed at corners of the x-ray emission window 133 in this embodiment.

The locations of the ultraviolet ray emitters 140 are not limited to the locations shown in FIGS. 3 and 4. However, in order to irradiate a wide area with high intensity ultraviolet rays, it is preferable that the ultraviolet ray emitters 140 be disposed at the x-ray emission window 133 side of the x-ray tube holder 130. The number of ultraviolet ray emitters 140 is not limited to four, but may be less than or more than four. The shape of the ultraviolet ray emitters 140 is not limited to a point-like shape, but may be a plate-like shape.

A visible light emitter (not shown) may be disposed around the ultraviolet ray emitters 140 of the x-ray tube holder 130. Visible light emitted from the visible light emitter may light up the area close to the hands of the radiological technologist during the preparation of an x-ray examination, for example. The visible light emitter is turned out when ultraviolet rays are emitted from the ultraviolet ray emitters 140.

The x-ray detector housing 150 houses an x-ray detector 151 as shown in FIG. 1. The x-ray detector 151 is, for example, a flat panel detector (FPD). The x-ray detector 151 detects x-rays emitted from the x-ray tube 131 and passing through a subject of examination P. The x-ray detector 151 sends a detection signal obtained by converting the detected x-rays to an electric charge corresponding to the amount of the detected x-rays to the processing circuitry 170.

The x-ray detector housing 150 is disposed to a bed 152, as shown in FIG. 2. In a horizontal x-ray examination, the x-ray tube holder 130 is moved to a position where the x-ray tube 131 faces the x-ray detector 151 included in the x-ray detector housing 150. The x-ray tube 131 then emits x-rays to the subject of examination P lying on the bed 152 in an x-ray emission operation that is instructed through the input interface 100.

The x-ray detector housing 150 may be mounted on an upright bar. In an x-ray examination which is performed while the subject is standing, the x-ray tube holder 130 is moved to a position at which the x-ray tube 131 faces the x-ray detector 151 of the x-ray detector housing 150. The x-ray tube 131 then emits x-rays to the subject of examination P standing in front of the upright bar in an x-ray emission operation instructed through the input interface 100.

The processing circuitry 170 controls the components of the x-ray diagnosis apparatus 1. The processing circuitry 170 performs a control function by executing a computer program stored in the storage 180. The processing circuitry 170 also has a contact portion detecting function 171, a route determining function 172, and an irradiation control function 173. The control functions of the processing circuitry 170 are not limited to the aforementioned functions, but may include, for example, a display control function for controlling the display 110.

The contact portion detecting function 171 corresponds to a contact portion detector, and detects a contact portion touched by a subject of detection that is at least one of the subject of examination P and the examination technician such as a radiological technologist during the x-ray examination, and a contact time during which the contact portion is touched. In the first embodiment, the contact portion detecting function 171 obtains an image taken by the optical camera 200, and analyzes the image to detect the contact portion and the contact time. For example, the contact portion detecting function 171 performs an edge (contour) processing on the image taken by the optical camera 200 to detect the subject of detection, and determines an area around the detected area as the contact portion. Furthermore, the contact portion detecting function 171 determines a period of time, in which the subject of detection is in the detected area in the taken image, as the contact time.

The route determining function 172 corresponds to a route determiner, and determines a route along which the x-ray tube holder 130 is moved to a position corresponding to the contact portion detected by the contact portion detecting function 171. For example, the route determining function 172 determines a route along which the x-ray tube holder 130 is moved based on position information of the supporter 210.

The irradiation control function 173 corresponds to an irradiation controller, and moves the x-ray tube holder 130 attached to the supporter 210 to the position corresponding to the contact portion based on the route determined by the route determining function 172 in the first embodiment. The irradiation control function 173 may autonomously move the x-ray tube holder 130 based on the contact portion detected by the contact portion detecting function 171 without relying on the route determining function 172. The irradiation control function 173 also controls the ultraviolet ray emitters 140 attached to the x-ray tube holder 130 to emit ultraviolet rays toward the contact portion during a period of time in which no x-ray examination is performed. The irradiation control function 173 may control the period of time in which the ultraviolet ray emitters 140 emit ultraviolet rays. This ultraviolet ray emitting time may be set depending on the contact time detected by the contact portion detecting function 171, for example. Specifically, the ultraviolet ray emitting time may be elongated as the contact time becomes longer, or the ultraviolet ray emitting time may have the same length as the contact time.

The storage 180 includes at least one of a semiconductor memory device such as a random access memory (RAM), an MRAM, a FRAM, or a flash memory, a hard disk, or an optical disc. The storage 180 may include a portable storage medium such as a universal serial bus (USB) memory or a digital versatile disc (DVD). The storage 180 stores a variety of programs used in the processing circuitry 170, data needed for executing the programs, and x-ray images. The programs include not only application programs but also an operating system (OS).

Figure 5:
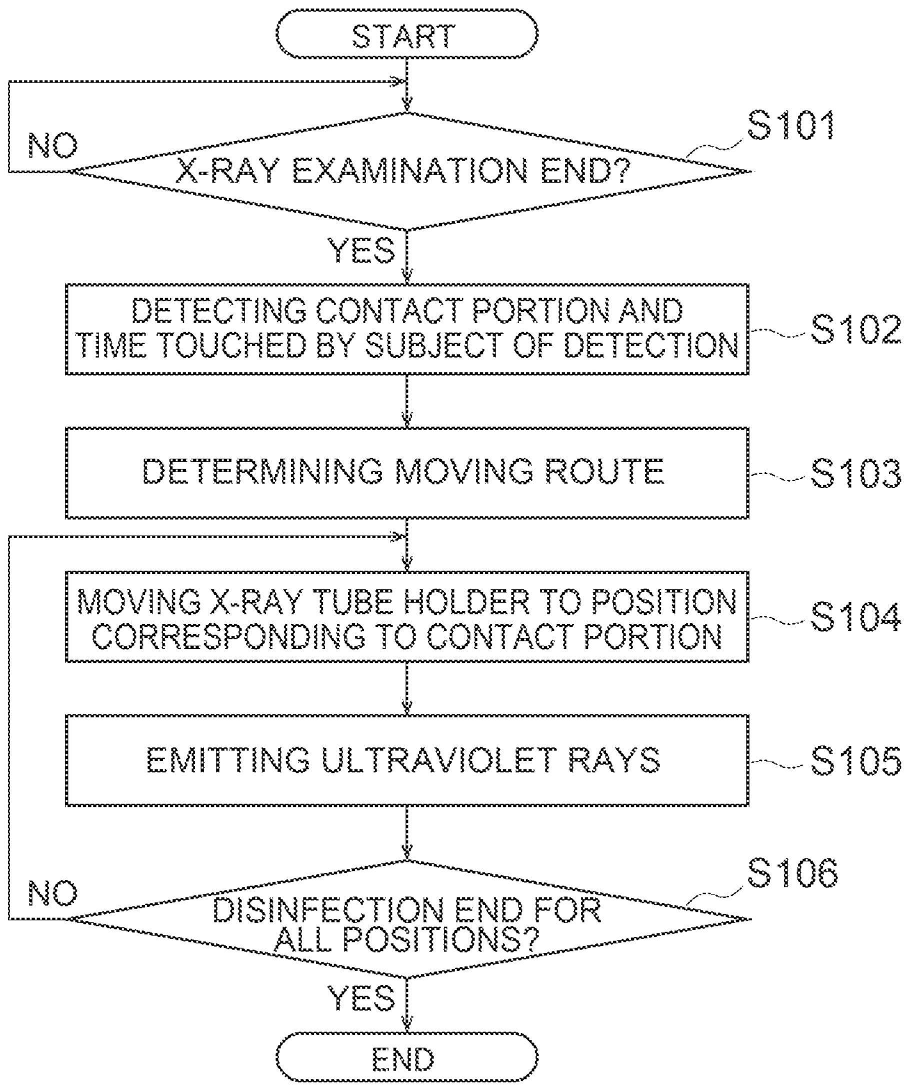
FIG. 5 is a flowchart of a disinfection operation according to the first embodiment.

FIG. 5 is a flowchart of a disinfection operation according to the first embodiment. Hereinafter, a disinfection operation of the x-ray diagnosis apparatus 1 described above will be described. The disinfection operation is performed during a period of time after an x-ray examination in the examination room 300 ends and before a next x-ray examination starts.

In the flowchart shown in FIG. 5, first the processing circuitry 170 determines whether an x-ray examination ends in the examination room 300 (step S101).

Subsequently, the contact portion detecting function 171 of the processing circuitry 170 detects the contact portion touched by the subject of detection and the contact time (step S102). The subject of detection is at least one of the subject of examination P and the examination technician. For example, during an (horizontal) x-ray examination using the x-ray detector housing 150 (horizontal table) shown in FIG. 2, the optical cameras 200 take images of the subject of examination P and the examination technician, and supply the taken images to the processing circuitry 170. The processing circuitry 170 controls the storage 180 to store the images supplied from the optical cameras 200. After the x-ray examination ends, the contact portion detecting function 171 detects the contact portion touched by the subject of examination P and the examination technician based on the images stored in the storage 180.

More specifically, the contact portion detecting function 171 detects the location of the subject of examination P on the bed 152 and the location of any place touched by the subject of examination P on the bed 152 during the x-ray examination (for example, the location of a portion of an assist handle of the bed 152 grabbed by the subject of examination P) as contact portions of the subject of examination. The contact portion detecting function 171 also detects the contact time during which the subject of examination P touches something. The contact portion detecting function 171 further detects a portion of the bed 152 and portions of peripheral devices disposed around the bed 152 touched by the examination technician as contact portions of the examination technician. The contact portion detecting function 171 also detects the contact time during which the examination technician touches something.

Subsequently, the route determining function 172 determines a moving route along which the x-ray tube holder 130 is moved to a position corresponding to the contact portion detected by the contact portion detecting function 171 (step S103). More specifically, the route determining function 172 determines a moving route along which the x-ray tube holder 130 is moved so that the ultraviolet ray emitters 140 are at positions corresponding to the contact portion detected in step S102. The positions corresponding to the contact portion here mean positions of the ultraviolet ray emitters 140 at which the ultraviolet ray emitters 140 may fully disinfect the contact portion with ultraviolet rays. Specifically, the positions allow the ultraviolet ray emitters 140 to face the contact portion at a distance less than 20 cm. If two or more contact portions are detected by the contact portion detecting function 171, the route determining function 172 determines a moving route passing through all of the positions corresponding to the contact portions. In such a case, the route determining function 172 selects a moving route having the shortest moving distance among possible moving routes passing through all of the positions corresponding to the contact portions. Furthermore, the route determining function 172 detects obstacles in the examination room 300, such as pillars, based on the images stored in the storage 180, and determines a moving route in which the obstacles are avoided. The processes of step S102 and step S103 may be performed during the x-ray examination, instead of being performed after the x-ray examination ends.

The irradiation control function 173 controls the supporter 210 so that the x-ray tube holder 130 may be moved along the moving route determined by the route determining function 172 to the position corresponding to the contact portion (step S104). For example, the x-ray tube holder 130 is moved to a position within 20 cm from the contact portion.

After the x-ray tube holder 130 is moved to the position corresponding to the contact portion, the irradiation control function 173 controls the ultraviolet ray emitters 140 to emit ultraviolet rays toward the contact portion (step S105). The area to which the ultraviolet rays are emitted may include not only the devices used in the x-ray examination such as the x-ray detector housing 150 (including the horizontal table or the upright bar) but also the floor and the walls of the examination room 300 near the devices, since the floor and the walls are preferably disinfected, too.

The irradiation control function 173 may use simulation information for emitted ultraviolet rays. The simulation information is a distribution of irradiation amount in the examination room 300 when ultraviolet rays are emitted from an ultraviolet ray emitter 140 on various irradiation conditions. As the irradiation amount increases, the disinfection effect improves. When the contact portion of the subject of examination P is specified by the contact portion detecting function 171, the irradiation control function 173 may determine an optimum irradiation area and irradiation time for disinfecting the specified contact portion based on the simulation information.

The aforementioned processes of moving the x-ray tube holder 130 (step S104) and emitting ultraviolet rays from the ultraviolet ray emitter 140 (step S105) are repeated until the disinfection is finished for all contact portions (step S106).

According to the first embodiment described above, ultraviolet rays are emitted at a short distance from the contact portion of the subject of detection (for example, the distance between the contact portion and the ultraviolet ray emitters 140 is less than 20 cm) in the examination room 300. As a result, the disinfection is concentratedly performed for the area that needs disinfection, instead of all areas of the examination room 300. This may shortens the time needed for disinfection. Since the ultraviolet rays are automatically emitted, no manual disinfection is needed. Therefore, the examination room 300 may be reliably disinfected.

[First Modification]

Figure 6A:
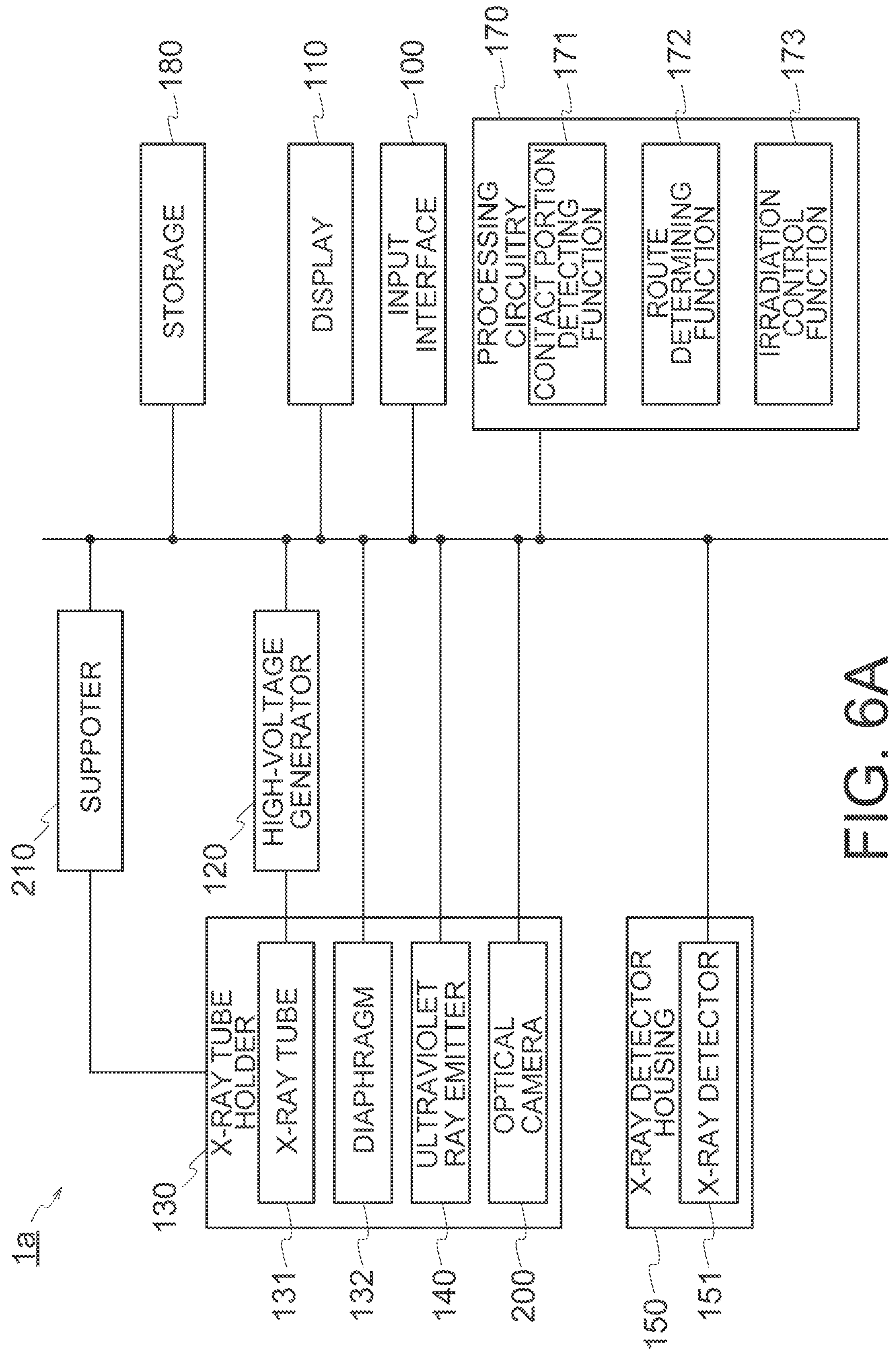
FIG. 6A is a block diagram showing a configuration of an x-ray diagnosis apparatus according to a first modification.

FIG. 6A is a block diagram showing a configuration of an x-ray diagnosis apparatus according to a first modification.

Figure 6B:
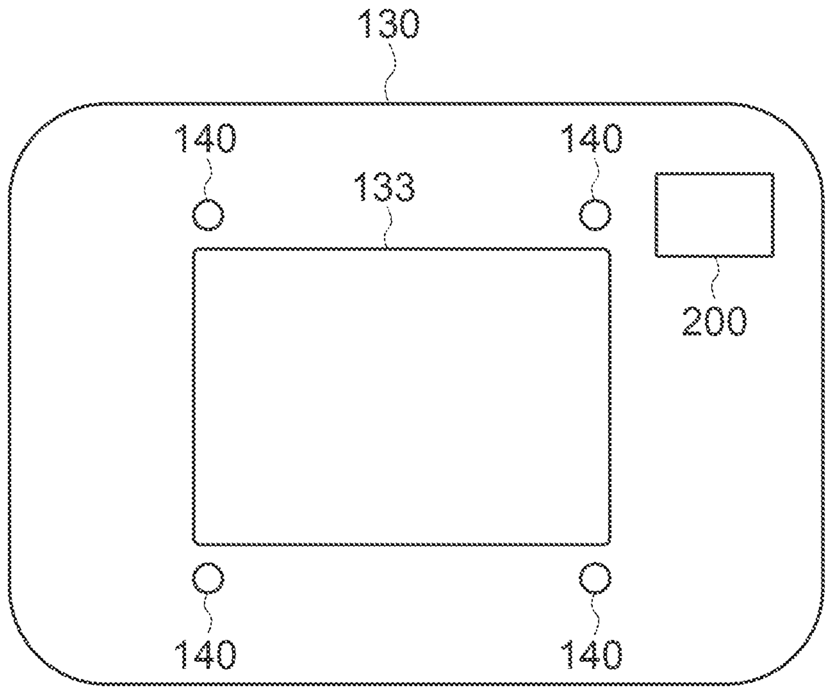
FIG. 6B is a front view of the x-ray tube holder according to the first modification, viewed from the side toward which x-rays are emitted.

FIG. 6B is a front view of the x-ray tube holder 130 according to the first modification, viewed from the side toward which x-rays are emitted. Elements that are common to those of the x-ray diagnosis apparatus 1 according to the first embodiment described above have the same reference numerals, and detailed descriptions of such elements are not provided.

As shown in FIGS. 6A and 6B, in the x-ray diagnosis apparatus 1*a* according to the first modification, the optical camera 200 is disposed to the x-ray tube holder 130. Specifically, as shown in FIG. 6B, the optical camera 200 is disposed to an area surrounding the x-ray emission window 133. The location of the optical camera 200 in the x-ray tube holder 130 is not limited to the location shown in FIG. 4, but may be any location at which an image of the subject of examination P may be taken during an x-ray examination.

During an x-ray examination, the x-ray tube holder 130 is located at a position facing the subject of examination P. As a result, the optical camera 200 disposed on the front face of the x-ray tube holder 130 may take images of the subject of examination P during the x-ray examination. Therefore, the contact portion detecting function 171 of the processing circuitry 170 may detect the contact portion and the contact time of the subject of examination P by analyzing the images taken by the optical camera 200, as in the first embodiment.

Thereafter, the route determining function 172 determines a moving route of the x-ray tube holder 130 based on the detection result of the contact portion detecting function 171, as in the first embodiment. Furthermore, the irradiation control function 173 causes the x-ray tube holder 130 to be moved along the moving route while the ultraviolet ray emitters 140 are emitting ultraviolet rays.

According to the first modification described above, the optical camera 200 is disposed to the x-ray tube holder 130. Therefore, images of the subject of examination P may be taken at a shorter distance than the distance in the first embodiment during an x-ray examination. As a result, the state of the subject of examination P during the x-ray examination may be more clearly imaged, and therefore the contact portion and the contact time may be more accurately detected.

[Second Modification]

Figure 7A:
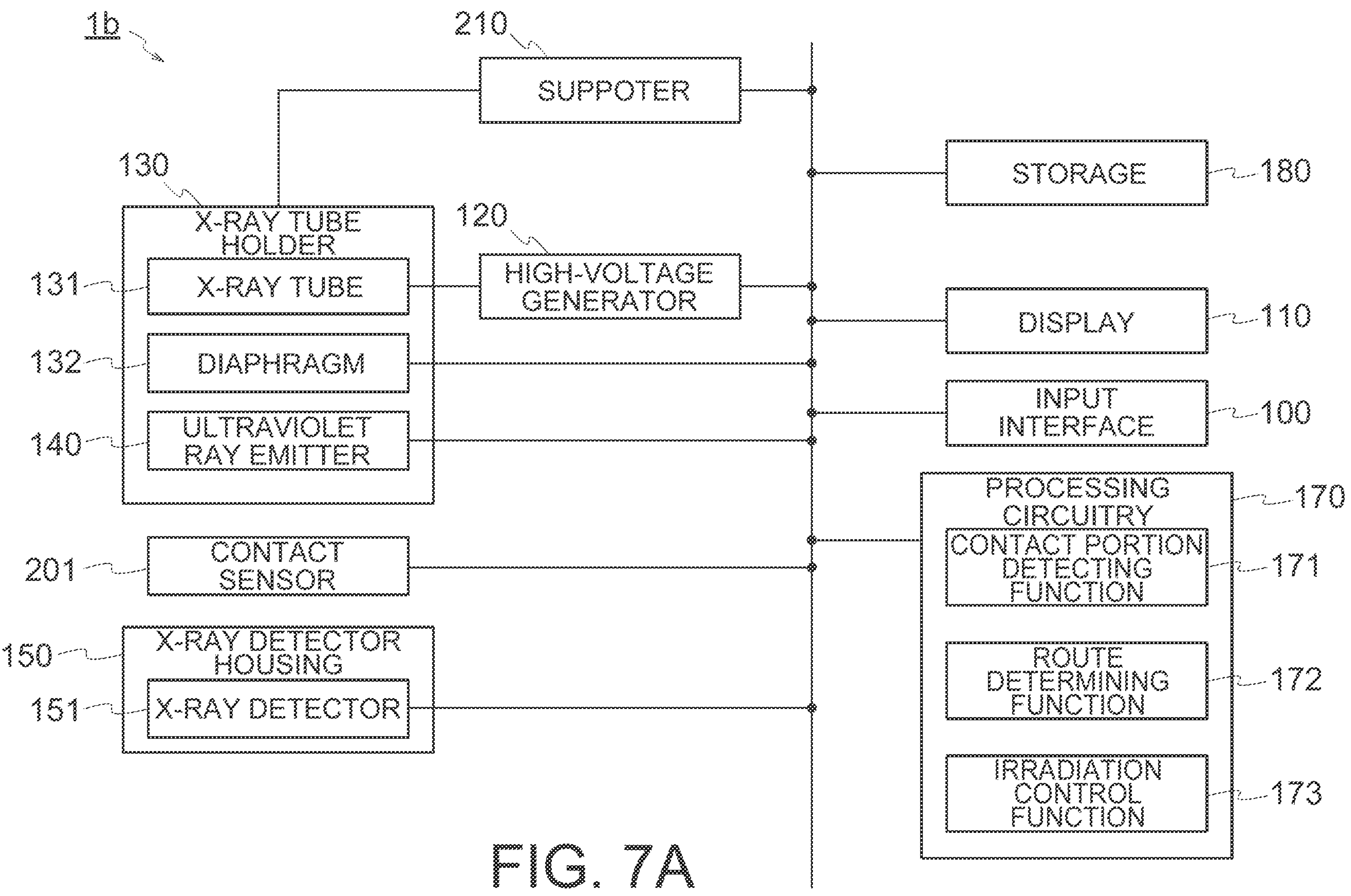
FIG. 7A is a block diagram showing a configuration of an x-ray diagnosis apparatus according to a second modification.
Figure 7B:
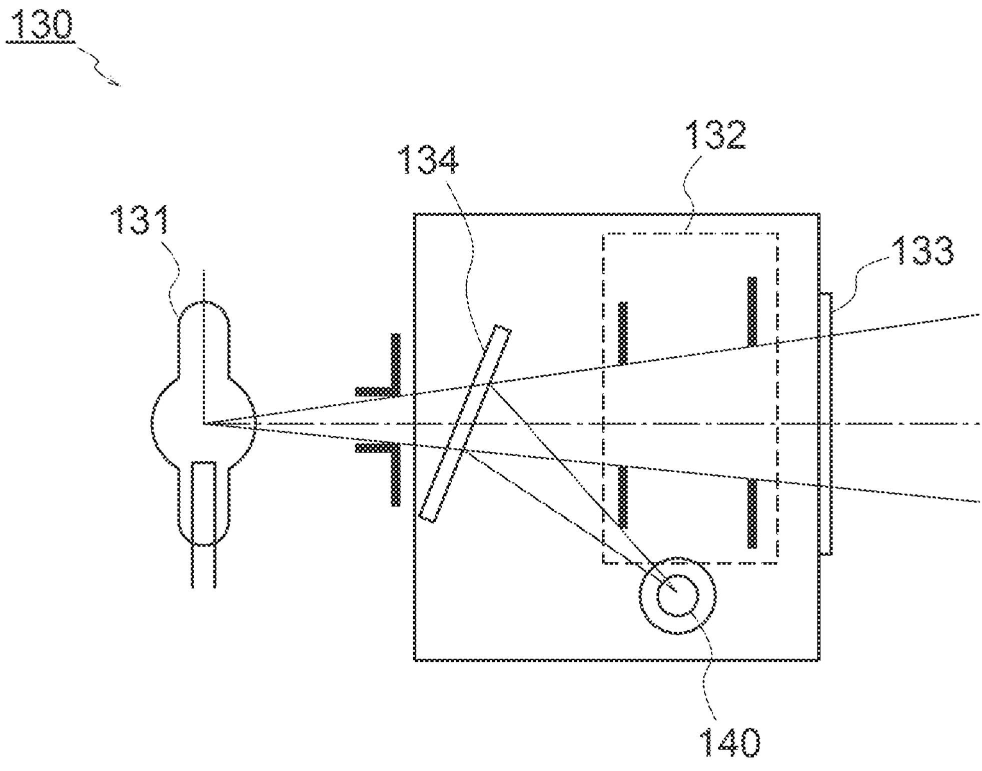
FIG. 7B is a diagram illustrating an example of an internal structure of an x-ray tube holder according to the second modification.

FIG. 7A is a block diagram showing a configuration of an x-ray diagnosis apparatus according to a second modification FIG. 7B is a diagram illustrating an example of an internal structure of an x-ray tube holder 130 according to the second modification. Elements that are common to those of the x-ray diagnosis apparatus 1 according to the first embodiment described above have the same reference numerals, and detailed descriptions of such elements are not provided.

As shown in FIG. 7A, the x-ray diagnosis apparatus 1*b* according to the second modification includes a contact sensor 201 instead of the optical camera 200. The contact sensor 201 includes, for example, a plurality of pressure sensors disposed to the bed 152 (see FIG. 2) of the x-ray detector housing 150. The contact portion detecting function 171 receives sensor detection information outputted from each pressure sensor.

As shown in FIG. 7B, the x-ray tube holder 130 according to the second modification includes a mirror 134 disposed between the x-ray tube 131 and the diaphragm 132. Furthermore, an ultraviolet ray emitter 140 is disposed within the x-ray tube holder 130 in a space between the x-ray tube 131 and the x-ray emission window 133. The space between the x-ray tube 131 and the x-ray emission window 133 herein means not only a spatial region between the x-ray tube 131 and the x-ray emission window 133 but also a surrounding region around the aforementioned spatial region, in which ultraviolet rays may be reflected on the mirror 134 so as to exit the x-ray tube holder 130 through the x-ray emission window 133. In the second modification, the ultraviolet ray emitter 140 may have a light illumination lamp in addition to the deep ultraviolet LED. Visible light rays from the light illumination lamp are emitted via the x-ray emission window 133, like x-rays. The emission of visible light rays helps the confirmation of the field of irradiation of x-rays, which are invisible light rays. The ultraviolet rays used for the disinfection are also emitted through the x-ray emission window 133. Thus, the ultraviolet ray emitter 140 may have two functions, the confirmation of the field of irradiation of x-rays and the disinfection.

During the x-ray examination according to the second modification, the x-rays emitted from the x-ray tube 131 reach the subject of examination P after passing through the mirror 134 and then passing through the diaphragm 132 and the x-ray emission window 133. Since the subject of examination P is lying in a supine position on the bed 152 during the x-ray examination, the pressure applied to a contact sensor 201 at a portion of the bed 152 in contact with the subject of examination P increases while the pressure applied to a contact sensor 201 disposed to a portion that is not in contact with the subject of examination P barely changes. When the x-ray examination ends and the subject of examination P rises from the bed 152, the pressure applied to the contact sensor 201 in contact with the subject of examination P decreases. Therefore, in the second modification, the contact portion detecting function 171 may obtain sensor detection information of the contact sensors 201 and detect the contact portion and the contact time of the subject of examination P based on pressure changes indicated in the obtained sensor detection information.

Thereafter, the route determining function 172 determines a moving route of the x-ray tube holder 130 based on the detection result of the contact portion detecting function 171, as in the first embodiment. Furthermore, the irradiation control function 173 moves the x-ray tube holder 130 along the moving route while the ultraviolet ray emitter 140 emits ultraviolet rays. The ultraviolet rays emitted from the ultraviolet ray emitter 140 are reflected on the mirror 134, pass through the diaphragm 132 and the x-ray emission window 133, and move toward the contact portion.

According to the second modification described above, the contact sensors 201 directly measure the contact portion of the subject of examination P. Therefore, the contact portion may be detected more accurately as compared to the first embodiment in which the contact portion is indirectly detected via the images taken by the optical camera 200. As a result, an area that needs disinfection by means of ultraviolet rays may be specified more precisely.

Furthermore, in the second modification, the ultraviolet rays from the ultraviolet ray emitter 140 are reflected on the mirror 134 and then emitted through the x-ray emission window 133. Therefore, both x-rays and ultraviolet rays are emitted through the x-ray emission window 133. Thus, there is no need to newly make a window for emitting ultraviolet rays in the x-ray tube holder 130, and the ultraviolet ray emitter 140 may be disposed within the x-ray tube holder 130.

[Third Modification]

Figure 8:
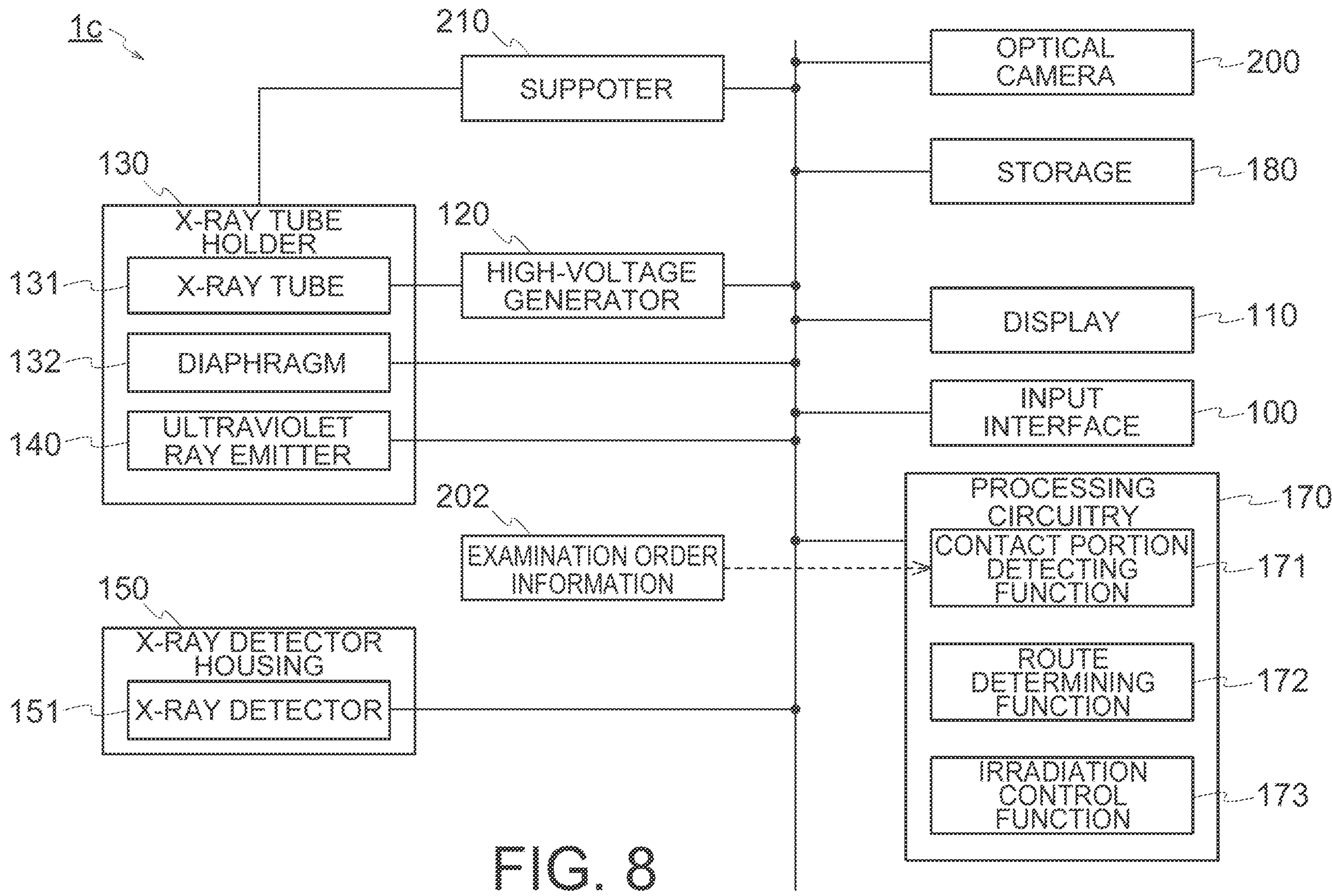
FIG. 8 is a block diagram showing a configuration of an x-ray diagnosis apparatus according to a third modification.

FIG. 8 is a block diagram showing a configuration of an x-ray diagnosis apparatus according to a third modification. Elements that are common to those of the x-ray diagnosis apparatus 1 according to the first embodiment described above have the same reference numerals, and detailed descriptions of such elements are not provided.

In the x-ray diagnosis apparatus 1*c* according to the third modification, the contact portion detecting function 171 of the processing circuitry 170 obtains examination order information 202 relating to an x-ray examination. The examination order information 202 is created when a doctor requests a radiological technologist, for example, to perform an x-ray examination, and includes such information as the date and time of the request, the date on which the requested examination is performed, the type of examination, the imaging method, the portion to be imaged, and the direction of the imaging.

The contact portion detecting function 171 detects the contact portion and the contact time based on the obtained examination order information 202. For example, the contact portion detecting function 171 estimates the contact portion and the contact time from the portion to be imaged and the direction of the imaging indicated in the examination order information 202.

Thereafter, the route determining function 172 determines a moving route of the x-ray tube holder 130 based on the detection result of the contact portion detecting function 171, as in the first embodiment. Furthermore, the irradiation control function 173 moves the x-ray tube holder 130 along the moving route while the ultraviolet ray emitter 140 emits ultraviolet rays.

According to the third modification described above, the contact portion detecting function 171 detects the contact portion and the contact time based on the examination order information 202. Therefore, the processing load of the contact portion detecting function 171 may be reduced as compared to the first embodiment in which the images taken by the optical camera 200 are processed.

Second Embodiment

Figure 9:
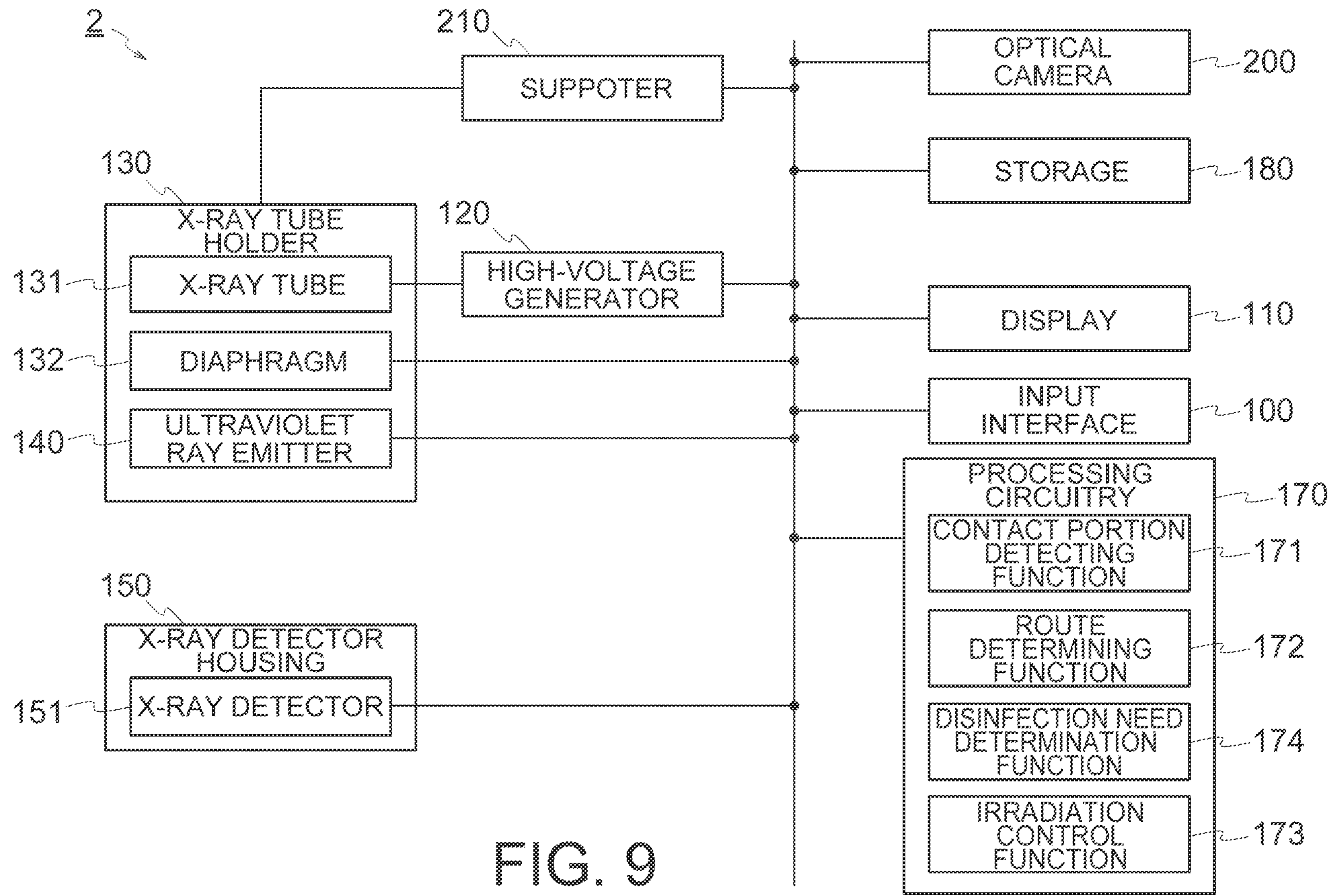
FIG. 9 is a block diagram showing a configuration of an x-ray diagnosis apparatus according to a second embodiment.

FIG. 9 is a block diagram showing a configuration of an x-ray diagnosis apparatus according to a second embodiment. Elements that are common to those of the x-ray diagnosis apparatus 1 according to the first embodiment described above have the same reference numerals, and detailed descriptions of such elements are not provided.

In the x-ray diagnosis apparatus 2 according to the second embodiment, the processing circuitry 170 further has a disinfection need determination function 174. The disinfection need determination function 174 obtains virus infection information of the subject of examination P when an x-ray examination ends. The virus infection information indicates whether the subject of examination P is infected with a virus at that time and the history of infection of the subject of examination P. The disinfection need determination function 174 determines whether the disinfection is needed based on the obtained virus infection information. If the subject of examination P is infected with a virus or if the virus carried by the subject of examination P is in a list of viruses that need disinfection, for example, the disinfection need determination function 174 determines that disinfection is needed. If the subject of examination P is not infected with a virus, or if the virus carried by the subject of examination P is not in the list of viruses that need disinfection, the disinfection need determination function 174 determines that disinfection is not needed.

If it is determined that disinfection is needed, the contact portion detecting function 171 detects the contact portion and the contact time based on the images taken by the optical camera 200. Subsequently, the route determining function 172 determines a moving route of the x-ray tube holder 130 based on the detection result of the contact portion detecting function 171. Furthermore, the irradiation control function 173 moves the x-ray tube holder 130 along the moving route while the ultraviolet ray emitters 140 emit ultraviolet rays.

If it is determined that disinfection is not needed, an x-ray examination is started without performing disinfection using ultraviolet rays.

According to the second embodiment described above, the disinfection need determination function 174 determines whether it is necessary to disinfect the examination room 300 based on the virus infection information. Since the ultraviolet ray emitter 140 does not emit ultraviolet rays when disinfection is not needed, a next x-ray examination can be started immediately. This may shorten the waiting time of the x-ray examination.

Third Embodiment

Figure 10:
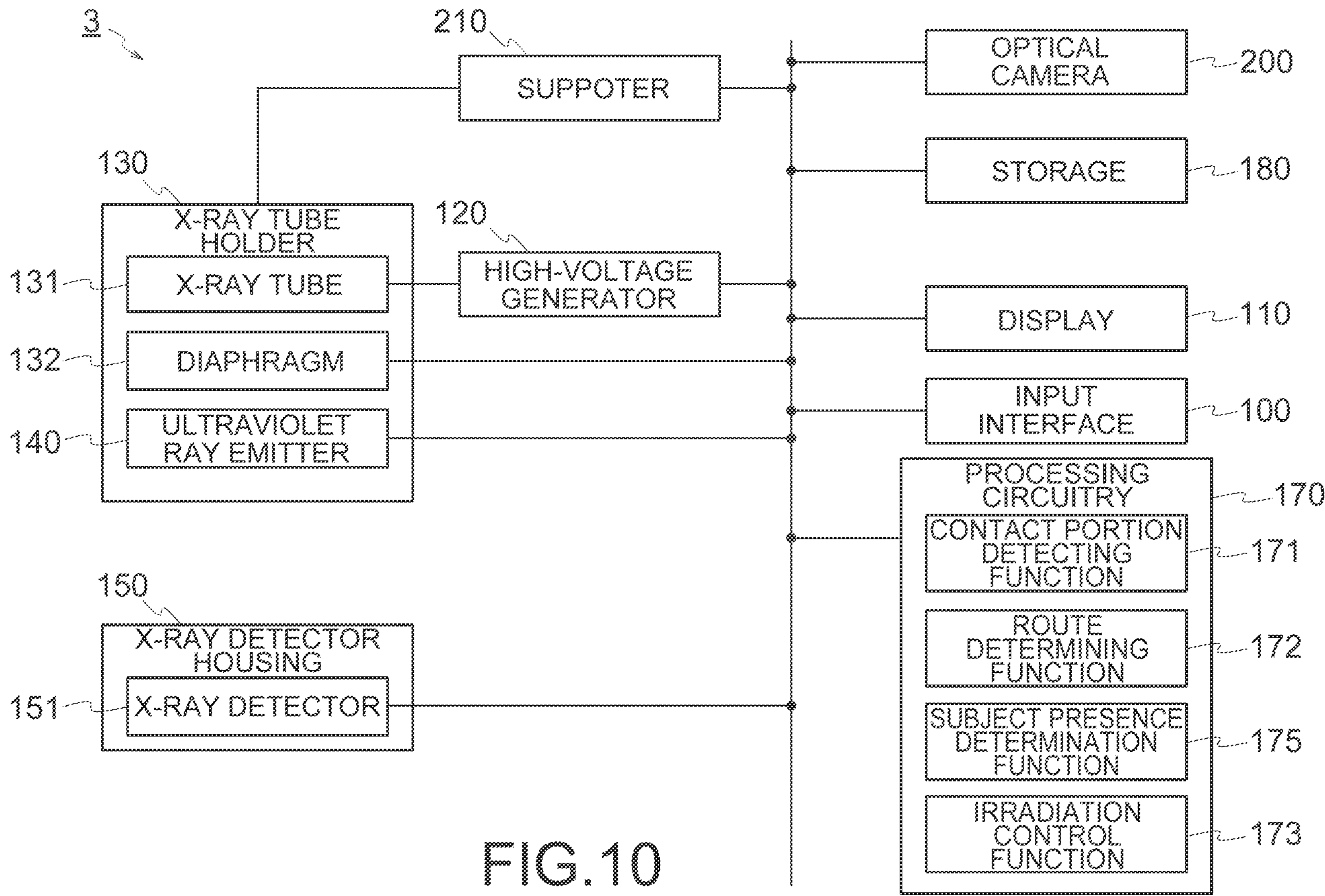
FIG. 10 is a block diagram showing a configuration of an x-ray diagnosis apparatus according to a third embodiment.

FIG. 10 is a block diagram showing a configuration of an x-ray diagnosis apparatus according to a third embodiment. Elements that are common to those of the x-ray diagnosis apparatus 1 according to the first embodiment described above have the same reference numerals, and detailed descriptions of such elements are not provided.

In the x-ray diagnosis apparatus 3 according to the third embodiment, the processing circuitry 170 further has a subject presence determination function 175. The subject presence determination function 175 determines whether a subject of detection is present around a contact portion in the examination room 300 when an x-ray examination ends. For example, the subject presence determination function 175 analyzes the images taken by the optical camera 200 to determine the presence of the subject of detection. If no subject of detection is in the taken images, the subject presence determination function 175 determines that no subject of detection is present around the contact portion. In this case, it is determined that no subject of detection is in the examination room 300.

If the subject presence determination function 175 determines that no subject of detection is present in the examination room 300, the display 110 displays a disinfection operation start button. When the radiological technologist uses the input interface 100 to click the disinfection operation start button, step S1 to step S106 of the disinfection operation in the first embodiment described above are performed.

The subject presence determination function 175 continuously analyzes the image information obtained from the optical camera 200 during the disinfection operation, and determines whether a subject of detection is present in the examination room 300. If a subject of detection enters the examination room 300 by mistake during the disinfection operation, for example, the subject of detection is detected by the subject presence determination function 175. In such a case, the irradiation control function 173 suspends the disinfection operation. In response to a suspension command from the irradiation control function 173, the supporter 210 stops the movement, and the ultraviolet ray emitter 140 stops emitting ultraviolet rays. After the emission of ultraviolet rays is stopped, when the subject presence determination function 175 confirms that no subject of detection is present in the examination room 300, the irradiation control function 173 restarts the disinfection operation, and the ultraviolet ray emitter 140 restarts emitting ultraviolet rays from the place which was being disinfected when the disinfection operation is suspended.

When all contact portions are disinfected in step S106, which was described above in the descriptions of the first embodiment, the display 110 displays a disinfection operation end button.

Subsequently, the irradiation control function 173 determines whether there is a non-disinfected area. For example, if there is an area that cannot be irradiated with ultraviolet rays due to the movement restriction of the supporter 210 in an area to which ultraviolet rays are emitted, the irradiation control function 173 determines the area that cannot be irradiated with ultraviolet rays as a non-disinfected area.

The irradiation control function 173 may determine whether there is a non-disinfected area using the simulation information of irradiated ultraviolet rays described in the descriptions of the first embodiment. In this case, for example, if there is an area in which the amount of irradiated ultraviolet rays is less than a reference value, the irradiation control function 173 determines such area as a non-disinfected area.

If there is a non-disinfected area, the display 110 displays a disinfection operation area button in order to suggest a manual disinfection using alcohol or the like. The display 110 also displays an image of the examination room 300, and the disinfection operation area button is displayed on a position in the image corresponding to the position that need a disinfection work in the examination room 300. In the third embodiment, the display 110 distinguishably displays a disinfected area, an area being disinfected, and a non-disinfected area.

When the disinfection work in the non-disinfected area is finished, the processing circuitry 170 allows a next examination to be performed. This allows the x-ray emission from the x-ray tube 131 of the x-ray tube holder 130.

In the third embodiment described above, when an x-ray examination ends, the subject presence determination function 175 of the processing circuitry 170 confirms that no person is present in the examination room 300. Therefore, the safety of the disinfection operation is improved. Furthermore, if a person enters the examination room 300 during a disinfection operation by mistake, the disinfection operation is suspended. Therefore, the safety of the disinfection operation is further improved. When there is a non-disinfected area, the disinfection operation area button is displayed to suggest a disinfection work. This may prevent the disinfection work from being unfinished.

Fourth Embodiment

A fourth embodiment is the same as the third embodiment except that an electronic lock is installed on a door for entering and leaving the examination room 300. A disinfection operation using the electronic lock will be described below.

In the fourth embodiment, when a previous examination ends, the subject presence determination function 175 determines whether a subject of detection is present around a contact portion in the examination room 300, as in the third embodiment.

If the subject presence determination function 175 determines that no subject of detection is present around a contact portion, the irradiation control function 173 locks the electronic lock. As a result, no one may enter the examination room 300.

After the electronic lock is locked, the disinfection operation is performed like the third embodiment. In the fourth embodiment, since the electronic lock is locked as described above, no person enters the examination room 300 by mistake during the disinfection operation. Therefore, unlike the third embodiment, the process of determining whether a subject of detection is present in the examination room 300 during a disinfection operation may be omitted in the fourth embodiment.

When all contact portions are disinfected, the display 110 displays a disinfection operation end button, as in the third embodiment. Subsequently, the irradiation control function 173 unlocks the electronic lock. Thereafter, the irradiation control function 173 determines whether there is a non-disinfected area as in the third embodiment.

If there is a non-disinfected area, the display 110 displays a disinfection operation area button as in the third embodiment. When the disinfection of the non-disinfected area is finished, the processing circuitry 170 allows a next examination to be performed.

In the fourth embodiment described above, the door of the examination room 300 is automatically locked during a disinfection operation. As a result, the disinfection operation is not interrupted, and the examination room 300 may be disinfected more speedily. Although an example of a locking and unlocking control of the electronic lock is described in the descriptions of the fourth embodiment, a display device, for example, showing information on whether the examination room 300 is being disinfected or has already been disinfected may be disposed outside the examination room 300 instead of locking and unlocking the electronic lock. This helps an examination technician waiting outside the examination room 300 know whether the examination room 300 is being disinfected or has already been disinfected based on the information displayed on the display device.

Fifth Embodiment

In a fifth embodiment, the area irradiated with ultraviolet rays is different from that of the first to fourth embodiments described above. A disinfection operation according to the fifth embodiment will be described below with reference to FIG. 11.

Figure 11:
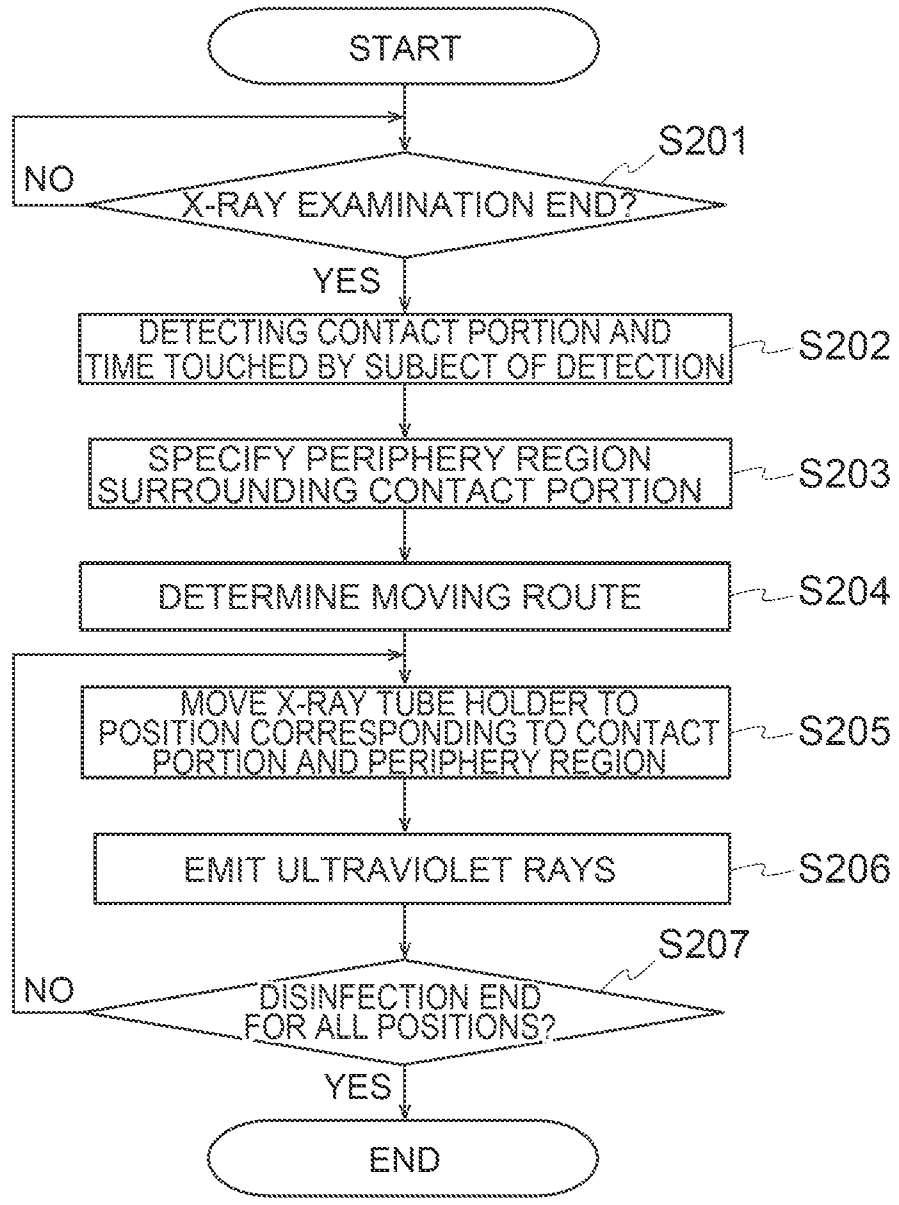
FIG. 11 is a flowchart of a disinfection operation according to a fifth embodiment.

FIG. 11 is a flowchart of the disinfection operation according to the fifth embodiment. In this flowchart, first the processing circuitry 170 determines whether an x-ray examination ends in the examination room 300 (step S201).

Subsequently, the contact portion detecting function 171 of the processing circuitry 170 detects a contact portion touched by a subject of detection and the contact time (step S202). The method of detecting the contact portion and the contact time is the same as that of the first embodiment, and therefore no detailed description thereof is provided.

The contact portion detecting function 171 then determines a periphery region surrounding a contact portion (step S203). The periphery region surrounding a contact portion will be described below with reference to FIG. 12.

Figure 12:
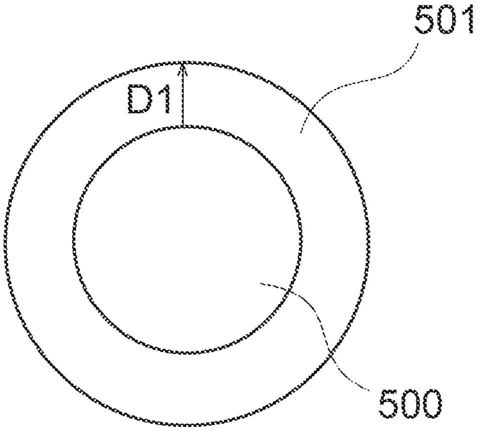
FIG. 12 is a schematic diagram for explaining a periphery region surrounding a contact portion.

FIG. 12 is a schematic diagram for explaining a periphery region surrounding a contact portion. A periphery region 501 shown in FIG. 12 surrounds a contact portion 500 detected by the contact portion detecting function 171 in step S202. For example, the contact portion detecting function 171 determines a region that is within a distance D1 from the periphery of the contact portion 500 as the periphery region 501, the distance D1 being a few tens of centimeters.

Returning to the flowchart shown in FIG. 11, after step S203 described above is finished, the route determining function 172 determines a moving route along which the x-ray tube holder 130 is moved to positions corresponding to the contact portion 500 and the periphery region 501 detected by the contact portion detecting function 171 (step S204). The position corresponding to the contact portion 500 is a position of the x-ray tube holder 130 suitable for fully disinfecting the contact portion 500 with ultraviolet rays emitted from the ultraviolet ray emitter 140, as described in the descriptions of the first embodiment. The position corresponding to the periphery region 501 is a position of the x-ray tube holder 130 suitable for fully disinfecting the periphery region 501 with ultraviolet rays emitted from the ultraviolet ray emitter 140.

If two or more periphery regions 501 are specified in step S203, a moving route passing through all of the positions corresponding to the periphery regions 501 is determined. In such a case, the route determining function 172 selects a moving route having the shortest distance among possible moving routes passing through all of the positions corresponding to the periphery regions 501. Furthermore, the route determining function 172 detects obstacles in the examination room 300, such as pillars, based on the images stored in the storage 180, and determines a moving route in which the obstacles are avoided. The processes of step S202 to step S204 may be performed during the x-ray examination, instead of being performed after the x-ray examination ends.

The irradiation control function 173 then controls the supporter 210 so that the x-ray tube holder 130 may be moved along the moving route determined by the route determining function 172 to the positions corresponding to the contact portion 500 and the periphery region 501 (step S205).

Every time the x-ray tube holder 130 is moved to a position corresponding to the contact portion 500 or the periphery region 501, the irradiation control function 173 controls the ultraviolet ray emitter 140 to emit ultraviolet rays toward the contact portion 500 or the periphery region 501 (step S206).

The process of moving the x-ray tube holder 130 (step S205) and the process of emitting ultraviolet rays from the ultraviolet ray emitter 140 (step S206) are repeated until the disinfection is finished for all contact portions 500 and all periphery regions 501 (step S207).

According to the fifth embodiment described above, the area irradiated with ultraviolet rays is expanded to cover not only the contact portion 500 of the subject of detection but also the periphery region 501. Therefore, the examination room 300 may be disinfected more reliably. Since the area irradiated with ultraviolet rays does not cover the entire area of the examination room 300 in the fifth embodiment, it may be possible to shorten the time needed for the disinfection.

Sixth Embodiment

A sixth embodiment is also different from the first to fourth embodiments since the area irradiated with ultraviolet rays is different. A disinfection operation according to the sixth embodiment will be described below with reference to FIG. 13.

Figure 13:
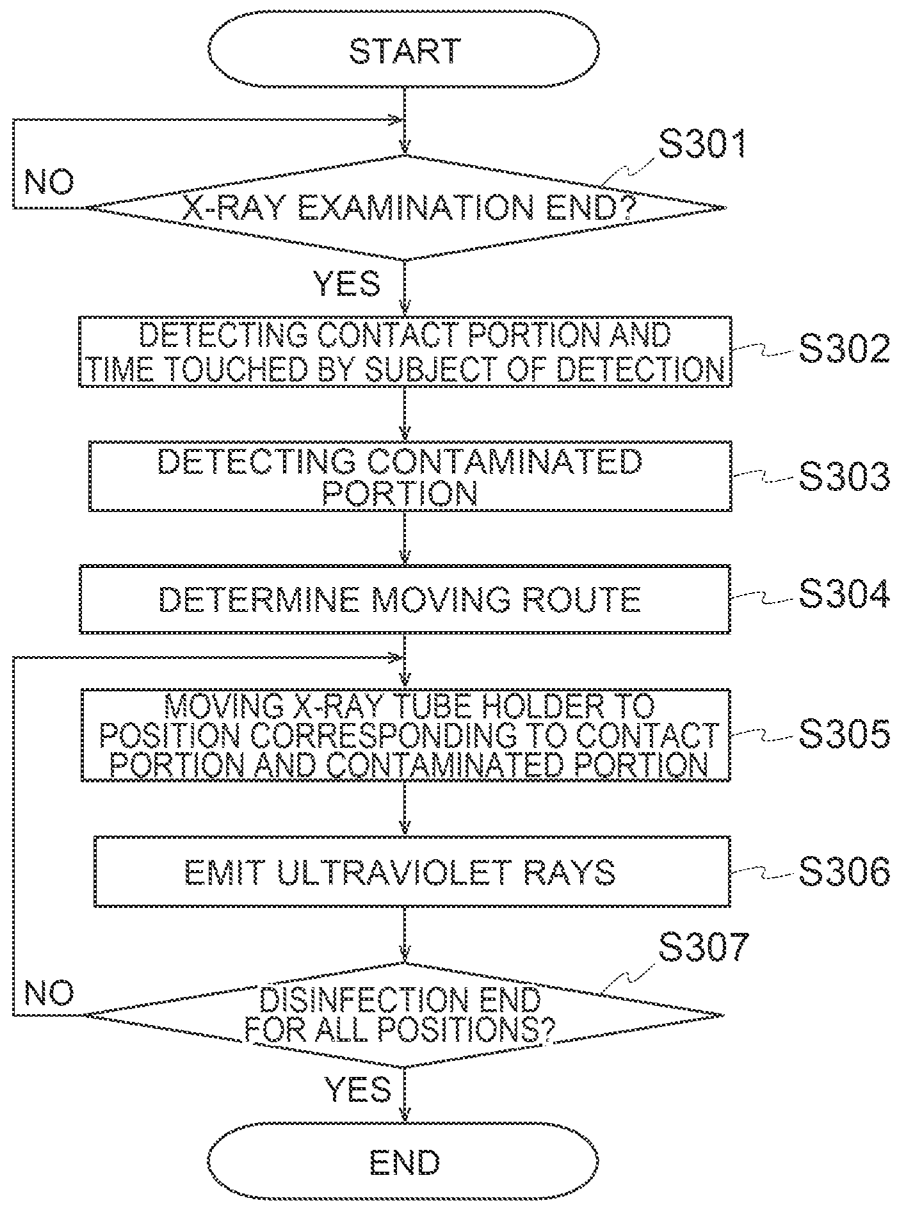
FIG. 13 is a flowchart of a disinfection operation according to a sixth embodiment.

FIG. 13 is a flowchart of the disinfection operation according to the sixth embodiment. In this flowchart, first the processing circuitry 170 determines whether an x-ray examination ends in the examination room 300 (step S301).

Subsequently, the contact portion detecting function 171 of the processing circuitry 170 detects the contact portion touched by the subject of detection and the contact time (step S302). The method of detecting the contact portion and the contact time is the same as that of the first embodiment, and therefore no detailed description thereof is provided.

The contact portion detecting function 171 then detects a contaminated portion (step S303). The contaminated portion will be described below with reference to FIG. 14.

Figure 14:
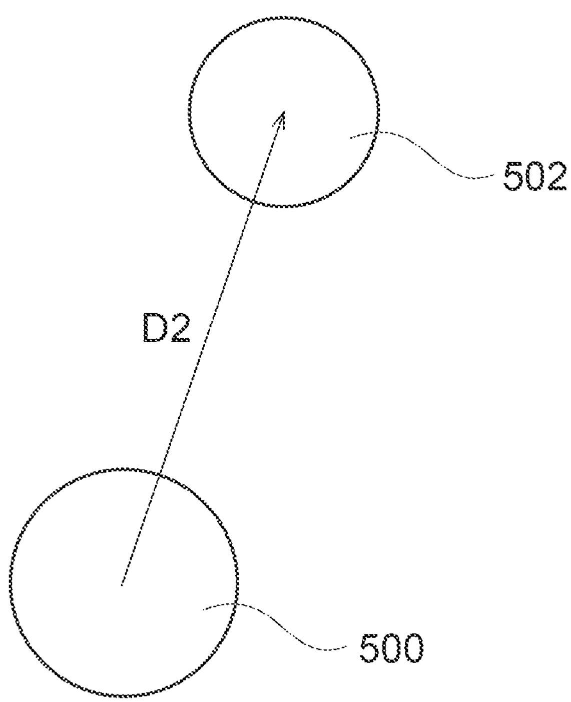
FIG. 14 is a schematic diagram for explaining a region around a contaminated portion.

FIG. 14 is a schematic diagram for explaining a contaminated portion. A contaminated portion 502 shown in FIG. 14 is a region contaminated with a spray of a cough or sneeze of the subject of detection. In step S303, the contact portion detecting function 171 analyzes the images taken by the optical camera 200 to determine whether the subject of detection coughs or sneezes. When a cough or sneeze of the subject of detection is confirmed, the contact portion detecting function 171 detects the contaminated portion 502. The contaminated portion 502 contaminated by the spray is considered to be away from the contact portion 500. Therefore, the contact portion detecting function 171 determines a region within a certain distance from a point that is away from the contact portion 500 by a distance D2 as the contaminated portion 502.

Returning to the flowchart shown in FIG. 13, when step S303 ends, the route determining function 172 determines a moving route along which the x-ray tube holder 130 is moved to positions corresponding to the contact portion 500 and the contaminated portion 502 detected by the contact portion detecting function 171 (step S304). The position corresponding to the contact portion 500 is a position of the x-ray tube holder 130 suitable for fully disinfecting the contact portion 500 with ultraviolet rays emitted from the ultraviolet ray emitter 140, as described in the descriptions of the first embodiment. The position corresponding to the contaminated portion 502 is a position of the x-ray tube holder 130 suitable for fully disinfecting the contaminated portion 502 with ultraviolet rays emitted from the ultraviolet ray emitter 140.

If two or more contaminated portions 502 are detected in step S303, a moving route passing through all of the positions corresponding to the contaminated portions 502 is determined. In such a case, the route determining function 172 selects a moving route having the shortest distance among possible moving routes passing through all of the positions corresponding to the contaminated portions 502. Furthermore, the route determining function 172 detects obstacles in the examination room 300, such as pillars, based on the images stored in the storage 180, and determines a moving route in which the obstacles are avoided. The processes of step S302 to step S304 may be performed during the x-ray examination, instead of being performed after the x-ray examination ends.

The irradiation control function 173 then controls the supporter 210 so that the x-ray tube holder 130 may be moved along the moving route determined by the route determining function 172 to the positions corresponding to the contact portion 500 and the contaminated portion 502 (step S305).

Every time the x-ray tube holder 130 is moved to a position corresponding to the contact portion 500 or the contaminated portion 502, the irradiation control function 173 controls the ultraviolet ray emitter 140 to emit ultraviolet rays toward the contact portion 500 or the contaminated portion 502 (step S306).

The process of moving the x-ray tube holder 130 (step S305) and the process of emitting ultraviolet rays from the ultraviolet ray emitter 14 (step S306) are repeated until the disinfection is finished for all contact portions 500 and all contaminated portions 502 (step S307).

According to the sixth embodiment described above, the area irradiated with ultraviolet rays covers not only the contact portion 500 of the subject of detection but also the contaminated portion 502 contaminated with a spray from the subject of detection. Therefore, the examination room 300 may be disinfected more reliably. Since the area irradiated with ultraviolet rays does not cover the entire area of the examination room 300 in the fifth embodiment, it may be possible to shorten the time needed for the disinfection.

Seventh Embodiment

Figure 15:
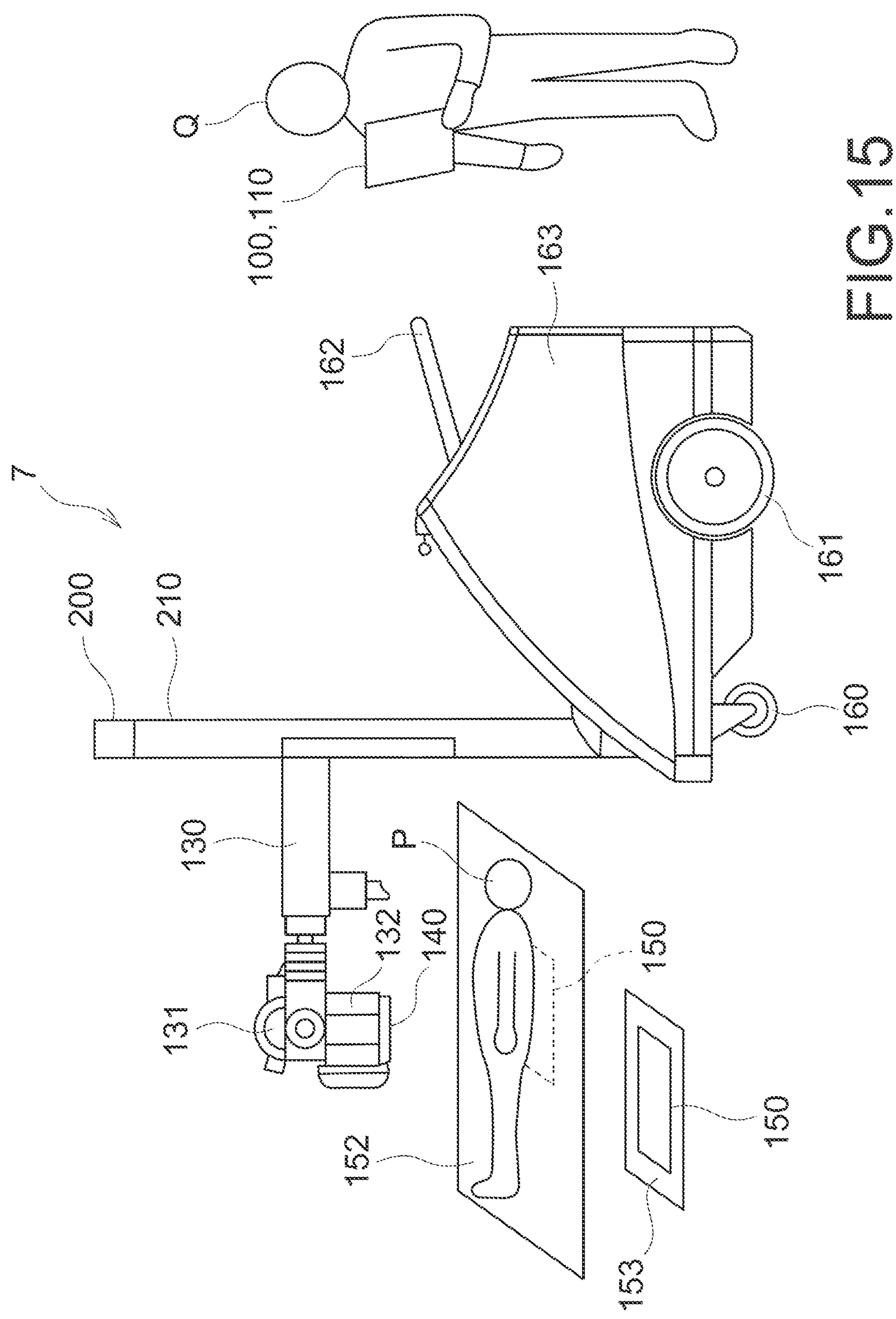
FIG. 15 is a schematic external view of an x-ray diagnosis apparatus according to a seventh embodiment.

FIG. 15 is a schematic external view of an x-ray diagnosis apparatus according to a seventh embodiment. Elements that are common to those of the x-ray diagnosis apparatus 1 according to the first embodiment described above have the same reference numerals, and detailed descriptions of such elements are not provided.

The x-ray diagnosis apparatus 7 shown in FIG. 15 is not fixed in the examination room 300, but is a mobile x-ray diagnosis apparatus. Therefore, the x-ray diagnosis apparatus 7 according to the seventh embodiment has front wheel 160, rear wheel 161, a handle 162, and a main body 163 in addition to the components of the x-ray diagnosis apparatus 1 according to the first embodiment.

The front wheel 160 and the rear wheel 161 are disposed under the main body 163. The front wheel 160 and the rear wheel 161 are each pivotable, and may be pairs of casters. The handle 162 is disposed to an upper portion of the main body 163. The x-ray diagnosis apparatus 7 may be moved when an examination technician Q pushes or pulls the handle 162.

The main body 163 houses such components as the high-voltage generator 120, the processing circuitry 170, and the storage 180 described in the descriptions of the first embodiment. In the seventh embodiment, the input interface 100 and the display 110 are disposed as a part of the functions of a tablet terminal.

Furthermore, in the x-ray diagnosis apparatus 7 according to the seventh embodiment, the supporter 210 is a bar-like member, for example, which stands upright in the front side (the front wheel 160 side) in the moving direction of the main body 163. The optical camera 200 is mounted on the top end of the supporter 210. The location of the optical camera 200 is not limited to the top end of the supporter 210, but may be the ceiling of a hospital room.

The x-ray tube holder 130 is formed of a resin or a metal. One end of the x-ray tube holder 130 is supported by the supporter 210 and the other end of the x-ray tube holder 130 holds the x-ray tube 131 and the diaphragm 132. The x-ray tube holder 130 is slidably connected to the supporter 210. The x-ray tube holder 130 may be configured to be extended or shortened in a direction perpendicular to the supporter 210.

When an x-ray examination is performed in a hospital room using the x-ray diagnosis apparatus 7 thus configured, the examination technician Q moves the x-ray diagnosis apparatus 7 by means of the handle 162 to the room of the subject of examination P. The examination technician Q moves the x-ray tube holder 130 so that the x-ray tube 131 faces a portion to be imaged of the subject of examination P. Furthermore, the examination technician Q makes an adjustment using a switch or a knob of the diaphragm 132 so that the portion to be imaged is within the field of irradiation. The x-ray detector housing 150 is then set between the portion to be imaged of the subject of examination P and the bed 152, and the x-ray examination is performed.

When the x-ray examination ends, the subject of examination P put the x-ray detector housing 150 on a table 153 disposed around the bed 152, for example. The x-ray detector housing 150 is touched by the subject of examination P and the examination technician Q, and therefore corresponds to the contact portion. In this case, the contact portion detecting function 171 detects the x-ray detector housing 150 put on the table 153 as a contact portion. In the seventh embodiment, the table 153 is shown in an image taken by the optical camera 200, for example, or the contact portion detecting function 171 may be provided with information in advance that the x-ray detector housing 150 is put on the table 153. Therefore, the contact portion detecting function 171 analyzes the image taken by the optical camera 200 to detect the position of the table 153, and specifies the detected position as the position of the contact portion. The method of detecting the contact portion is not limited to the above method, but may be a different method.

The route determining function 172 then determines a moving route along which the x-ray tube holder 130 is moved to a position corresponding to the x-ray detector housing 150.

Subsequently, the irradiation control function 173 moves the x-ray tube holder 130 to the position corresponding to the x-ray detector housing 150 based on the moving route determined by the route determining function 172, as in the first embodiment.

Thereafter, the irradiation control function 173 controls the ultraviolet ray emitter 140 to emit ultraviolet rays toward the x-ray detector housing 150 in order to disinfect the x-ray detector housing 150.

According to the seventh embodiment described above, ultraviolet rays are emitted toward the x-ray detector housing 150, which is the contact portion, within a short distance. Therefore, the concentrated disinfection may be performed not for the entire hospital room but for a portion that needs disinfection. This shortens time needed for the disinfection. Since the ultraviolet rays are automatically emitted from the ultraviolet ray emitter 140, no manual disinfection is needed. Therefore, the x-ray detector housing 150 may be reliably disinfected. Although the x-ray detector housing 150 is put on the table 153 in the seventh embodiment, the location of the x-ray detector housing 150 is not limited to the table 153. The x-ray detector housing 150 may be located at any place as long as the subject of examination P lying on the bed 152 is not irradiated with ultraviolet rays emitted from the ultraviolet ray emitter 140, and within the range in which the x-ray tube holder 130 may be moved.

In the seventh embodiment, the x-ray diagnosis apparatus 7 is a mobile x-ray diagnosis apparatus. Unlike the x-ray diagnosis apparatuses of fixed type described in the descriptions of the first to sixth embodiments, the mobile x-ray diagnosis apparatus may be used in a hospital room. Therefore, the load of a patient may be reduced since it is not necessary to move the patient.

According to at least one of the embodiments described above, disinfection may be reliably performed in a short time.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fail within the scope and spirit of the inventions.

The invention claimed is:

1. An x-ray diagnosis apparatus, comprising:

an x-ray tube holder configured to hold an x-ray tube;

a supporter configured to movably support the x-ray tube holder;

a plurality of ultraviolet ray emitters configured to emit ultraviolet rays and disposed on the x-ray tube holder;

a contact portion detector configured to detect a contact portion touched by a subject of detection, which is at least one of a subject of examination and an examination technician; and an irradiation controller configured to control the supporter to move the x-ray tube holder to a position corresponding to the contact portion, and configured to control the plurality of ultraviolet ray emitters to emit the ultraviolet rays toward the contact portion, wherein the contact portion detector is further configured to detect a contact time during which the subject of detection touches the contact portion, the irradiation controller is further configured to control the plurality of ultraviolet ray emitters to emit the ultraviolet rays based on an irradiation time corresponding to the detected contact time, the irradiation time is set to be elongated as the detected contact time becomes longer, the plurality of ultraviolet ray emitters is arranged around an x-ray emission window of the x-ray tube holder, and the contact portion detector is further configured to obtain pressure values detected by a plurality of pressure sensors disposed on a bed, and detect the contact portion based on the detected pressure values.

2. The x-ray diagnosis apparatus according to claim 1, further comprising processing circuitry configured to determine a route for moving the x-ray tube holder to the position corresponding to the contact portion, wherein the irradiation controller is further configured to control the supporter to move along the determined route.

3. The x-ray diagnosis apparatus according to claim 1, wherein the contact portion detector is further configured to detect the contact portion touched by the subject of detection while the x-ray examination is performed, and wherein the irradiation controller is further configured to control the plurality of ultraviolet ray emitters to emit the ultraviolet rays toward the contact portion while the x-ray examination is not performed.

4. The x-ray diagnosis apparatus according to claim 1, wherein the contact portion detector is further configured to obtain examination order information with respect to the x-ray examination, and detect the contact portion based on the obtained examination order information.

5. The x-ray diagnosis apparatus according to claim 1, further comprising processing circuitry configured to obtain infection information with respect to the subject of examination, and determine whether disinfection is needed based on the infection information, wherein the irradiation controller is further configured to control the plurality of ultraviolet ray emitters to emit the ultraviolet rays toward the contact portion based on a determination result of the disinfection need determiner.

6. The x-ray diagnosis apparatus according to claim 1, further comprising processing circuitry configured to determine whether the subject of detection is present around the contact portion after the x-ray examination is performed, wherein the irradiation controller is further configured to control the plurality of ultraviolet ray emitters to emit the ultraviolet rays toward the contact portion based on a determination result of the processing circuitry.

7. The x-ray diagnosis apparatus according to claim 2, wherein when the contact portion detector detects two or more contact portions, the processing circuitry is further configured to select a moving route that has a shortest moving distance among moving routes passing through all of the contact portions.

8. The x-ray diagnosis apparatus according to claim 1, wherein the contact portion detector is further configured to specify a periphery region surrounding the contact portion, and wherein the irradiation controller is further configured to control the supporter to move the x-ray tube holder to positions corresponding to the contact portion and the periphery region, and control the plurality of ultraviolet ray emitters to emit the ultraviolet rays toward the contact portion and the periphery region.

9. The x-ray diagnosis apparatus according to claim 1, wherein the contact portion detector is further configured to detect a contaminated portion that is at a distance from the contact portion and is contaminated by the subject of detection, and wherein the irradiation controller is further configured to control the supporter to move the x-ray tube holder to positions corresponding to the contact portion and the contaminated portion, and control the plurality of ultraviolet ray emitters to emit the ultraviolet rays toward the contact portion and the contaminated portion.

10. The x-ray diagnosis apparatus according to claim 1, wherein the x-ray diagnosis apparatus is movable to a hospital room of the subject examination by the examination technician, and wherein the contact portion detector is further configured to detect the contact portion in the hospital room.

11. A disinfection method using an x-ray diagnosis apparatus, the method comprising:

obtaining pressure values detected by a plurality of pressure sensors disposed on a bed;

detecting a contact portion touched by a subject of detection, which is at least one of a subject of examination and an examination technician, and a contact time during which the subject of detection touches the contact portion, based on the obtained pressure values;

moving a supporter that movably supports an x-ray tube holder to a position corresponding to the contact portion; and controlling a plurality of ultraviolet ray emitters arranged around the x-ray emission window of the x-ray tube holder to emit ultraviolet rays toward the contact portion based on an irradiation time corresponding to the detected contact time, wherein the irradiation time is set to be elongated as the detected contact time becomes longer.

* * * * *